United States Patent [19]
Debbas

[11] Patent Number: 5,662,674
[45] Date of Patent: *Sep. 2, 1997

[54] APPARATUS FOR LOCATING A BREAST MASS

[76] Inventor: Elie Debbas, 800 Southern Ave., SE. Suite 407, Washington, D.C. 20032

[*] Notice: The term of this patent shall not extend beyond the expiration date of Pat. No. 4,966,583.

[21] Appl. No.: 466,140

[22] Filed: Jun. 6, 1995

Related U.S. Application Data

[60] Continuation of Ser. No. 181,026, Jan. 14, 1994, Pat. No. 5,445,645, which is a division of Ser. No. 948,320, Sep. 22, 1992, Pat. No. 5,301,682, which is a division of Ser. No. 604,092, Oct. 29, 1990, Pat. No. 5,183,463, which is a continuation-in-part of Ser. No. 305,965, Feb. 3, 1989, Pat. No. 4,966,583.

[51] Int. Cl.⁶ .................................................. A61B 17/34
[52] U.S. Cl. .......................... 606/192; 606/185; 128/737; 604/96
[58] Field of Search .................................... 606/192, 193, 606/194, 196, 197, 185; 604/96, 100, 103, 97, 98, 99, 101, 102; 128/753, 754, 737

[56] References Cited

U.S. PATENT DOCUMENTS

| | | | |
|---|---|---|---|
| 2,001,638 | 5/1935 | Tomsjo | 128/347 |
| 2,705,949 | 4/1955 | Silverman | 128/2 |
| 3,039,468 | 6/1962 | Price . | |
| 3,154,077 | 10/1964 | Cannon | 128/325 |
| 3,515,137 | 6/1970 | Santomieri | 128/214.4 |
| 3,598,119 | 8/1971 | White | 128/215 |
| 3,634,924 | 1/1972 | Blake et al. | 29/447 |
| 3,680,544 | 8/1972 | Shinnick et al. | 604/158 X |
| 3,833,003 | 9/1974 | Taricco | 128/347 |
| 3,890,970 | 6/1975 | Gullen | 128/215 |
| 3,952,742 | 4/1976 | Taylor | 128/172.1 |
| 3,961,632 | 6/1976 | Moossun | 600/12 X |
| 4,007,732 | 2/1977 | Kvavle et al. | 128/2 B |
| 4,083,369 | 4/1978 | Sinnreich | 604/174 X |
| 4,240,433 | 12/1980 | Bordow . | |
| 4,315,512 | 2/1982 | Fogarty . | |
| 4,465,072 | 8/1984 | Taheri . | |
| 4,571,239 | 2/1986 | Heyman | 604/54 |
| 4,645,491 | 2/1987 | Evans | 604/158 |
| 4,682,606 | 7/1987 | DeCaprio | 128/754 |
| 4,819,664 | 4/1989 | Nazari | 128/207.15 |
| 4,968,298 | 11/1990 | Michelson | 604/36 |
| 4,973,305 | 11/1990 | Goltzer | 604/158 X |
| 4,976,725 | 12/1990 | Chin et al. | 606/192 X |
| 5,024,655 | 6/1991 | Freeman et al. | 604/53 |
| 5,419,765 | 5/1995 | Weldon et al. | 604/96 |

FOREIGN PATENT DOCUMENTS

| | | |
|---|---|---|
| 2477005 | 9/1981 | France . |
| 2480127 | 10/1981 | France . |
| 2565815 | 12/1985 | France . |

Primary Examiner—Michael H. Thaler
Attorney, Agent, or Firm—Burns, Doane, Swecker & Mathis, L.L.P.

[57] ABSTRACT

A mass localization device includes a catheter and a needle. In one embodiment, the catheter includes inner and outer walls spaced from each other and creating a gap between the walls extending along substantially the entire length of the catheter. The distal portion of the outer wall includes an inflatable balloon. In use, the balloon is positioned proximate the mass and inflated to make the mass palpable. An incision to the mass can be achieved by the shortest possible distance since the mass is made palpable.

7 Claims, 3 Drawing Sheets

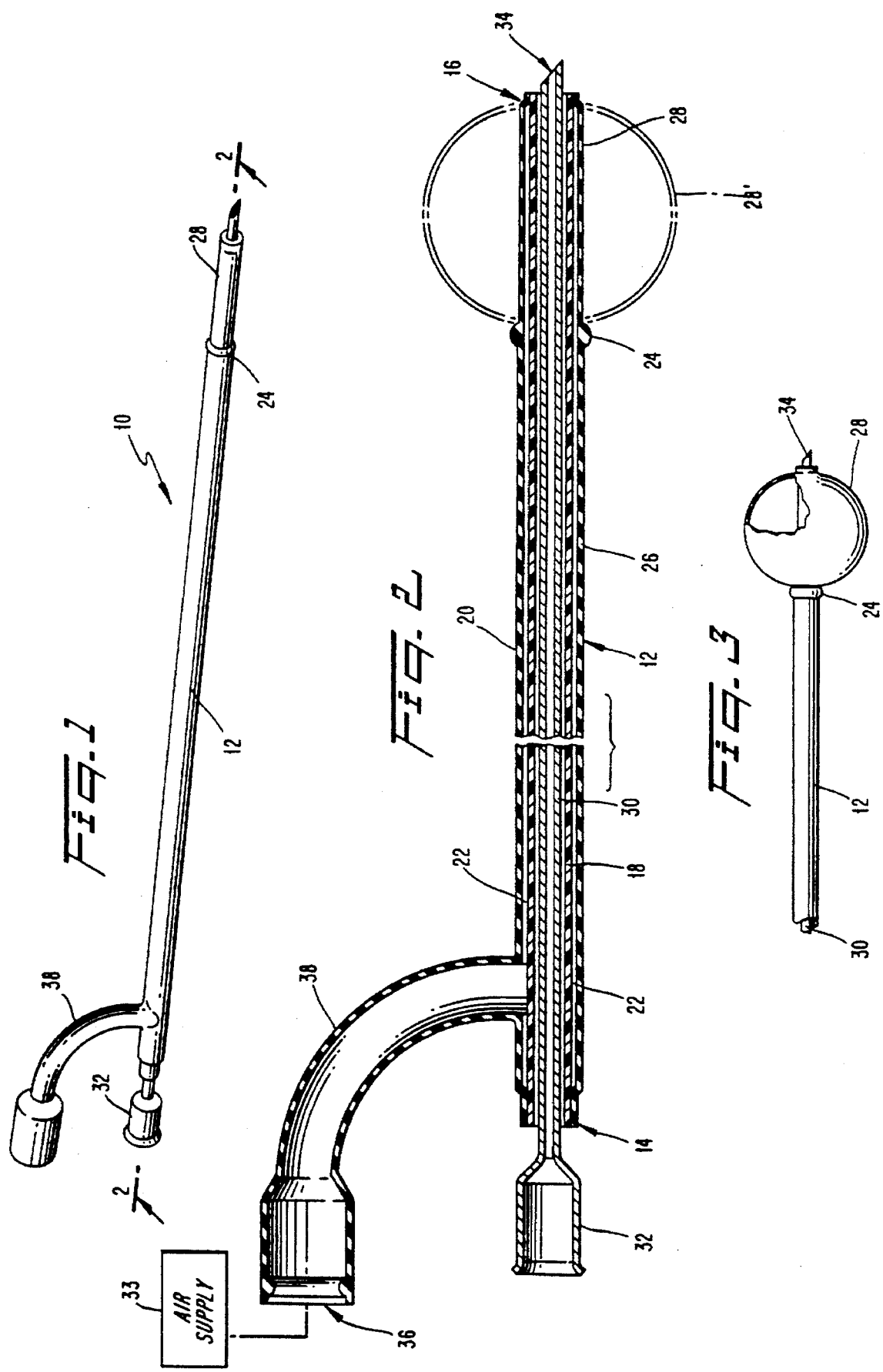

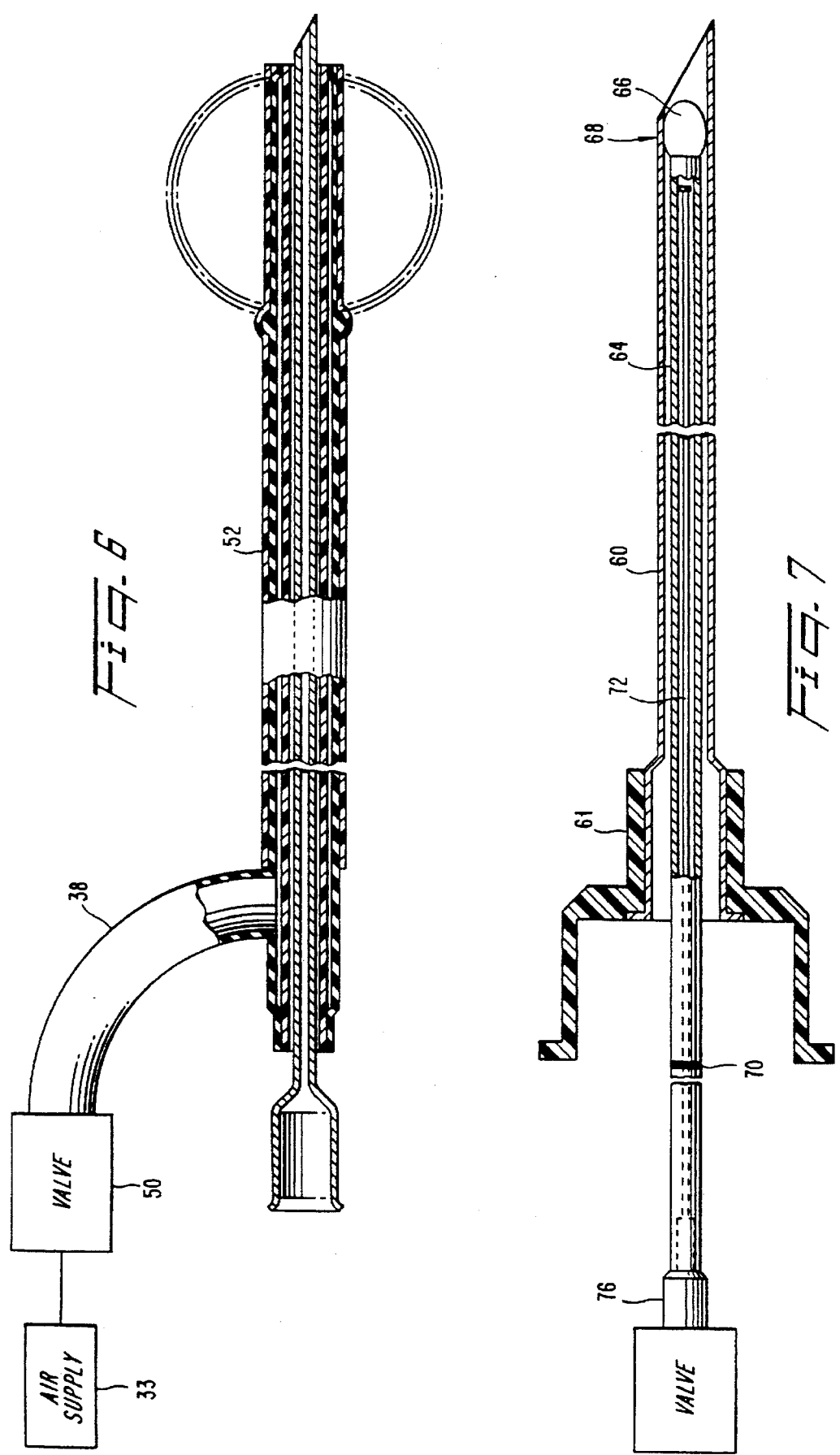

APPARATUS FOR LOCATING A BREAST MASS

This application is a continuation of application Ser. No. 08/181,026, filed Jan. 14, 1994, now U.S. Pat. No. 5,445,645 which is a divisional of application Ser. No. 07/948,320, filed Sep. 22, 1992, now U.S. Pat. No. 5,308,682 which is in turn a divisional application of application Ser. No. 07/604,092, filed Oct. 29, 1990, now U.S. Pat. No. 5,183,463, which is a continuation-in part of application Ser. No. 07/305,965, filed Feb. 3, 1989 now U.S. Pat. No. 4,966,583.

FIELD OF THE INVENTION

The present invention relates to a medical instrument for locating a mass in body tissue so that the mass may be accessed or removed by the most direct or most appropriate incision from the epidermal layer to the mass.

BACKGROUND OF THE INVENTION

Locating masses or tumors in human tissue is necessary for a biopsy of the suspicious mass and subsequent removal. Sometimes it is possible to locate a mass merely by touching the skin above and around the suspicious area. However, often the mass is too small to be noticed by hand or is located in fatty tissue that interferes with determining the precise location of the mass. A specific example of the latter case is the location of small breast masses or calcifications.

Typically, the precise location of these types of masses can only be determined by x-ray analysis, using specialized instrumentation prior to a surgical operation to locate the mass to be removed. Typically, a very thin needle is inserted into the breast down to the mass under x-ray control (mammography). Once it is determined by x-ray control that the tip of the needle is located at the mass site, the patient is transported to an operating room, where the surgeon creates an incision in the breast by following along the path of the inserted needle with a scalpel until reaching the mass. This method often involves a very long incision and increases the risk of post-operative infection.

An alternate method of creating an incision to gain access to or remove a breast mass is to study x-rays of the breast mass taken from various angles. Based upon experience and notional extrapolation of the views from different angles of the breast mass, an incision is made in an attempt to cut along the most direct path to the mass.

Several devices exist for localizing masses in human tissue. See, for example, U.S. Pat. Nos. 4,682,606 to DeCaprio, 3,890,970 to Gullen, and 3,598,119 to White.

The DeCaprio patent discloses a surgical needle which is inserted into a located mass and encircled by a cork screw device. The cork screw device is twisted around the mass until the tip of the worm of the screw is just beyond the furthest side of the mass. Thereafter, the handle of the cork screw device is withdrawn and a guiding extension rod is replaced to direct the surgeon to the depth of the mass in the patient's tissue. Then, a cutting instrument is inserted over the extension rod for removing the mass from the tissue.

The Gullen patent discloses a surgical cannula for delivery of paracervical anaesthesia. The cannula includes a catheter having a closed distal end with a perforated membrane. The distal end is firm and sharp enough to be inserted into body tissue to a predetermined depth, as limited by a stop member. A thin membranous ballooning portion is provided proximate the distal end of the catheter for expansion upon application of a fluid pressure within the catheter to lock the cannula in place in the tissue. The device is left in the tissue of the patient by the ballooning portion to provide periodic supply of fluid anaesthesia during a surgical procedure.

Similar to the patent to Gullen, the White patent discloses a medical instrument for use in gynecological procedures to allow the administration of a pardcervical block, continuously or intermittently, with only a single placement. The device comprises an elongated hollow tube having an open distal end and receiving a needle for guiding the device into tissue. An inflatable bladder is provided near the distal end of the hollow tube for retaining the device in the tissue and minimizing trauma associated with the procedure.

The prior art devices discussed above provide a procedure for retaining a catheter type instrument in the tissue of a patient, but fail to provide a procedure for precisely identifying a mass within the tissue. Moreover, the prior art devices are of an insufficient size to accurately locate a mass within breast tissue prior to surgery.

SUMMARY OF THE INVENTION

It is a primary object of the present invention to provide a device for accurately locating a mass within breast tissue prior to a surgical procedure for taking a biopsy of, or removing the mass.

According to one embodiment of the present invention, a catheter has proximal and distal open ends for receiving a hollow needle insertable into the catheter. An inflatable balloon is provided at the distalmost end of the catheter for expansion around the catheter at the distal end of the catheter. A source of sterile fluid (such as air or saline solution) is connected to the catheter adjacent the proximal end of the catheter, and has a separate port connection to the catheter.

Preferably, the inflatable balloon is formed as an outer layer or sheath extending along the length of the catheter. The distalmost end of the outer layer forming the inflatable balloon has a smaller thickness than the remainder of the outer layer. As such, upon the supply of fluid, the distal end of the outer layer expands, while the remaining portion of the outer layer remains flush with the periphery of the catheter.

With the balloon deflated and flush with the periphery of the catheter, a hollow needle is inserted to extend beyond the distal end of the catheter, and the device is inserted into the tissue to a position adjacent the mass to be located. Typically, this is performed under the control of x-ray (mammography) to precisely locate the mass. Once the mass is located and the combined catheter and needle is moved adjacent to the mass, local anesthetic is applied through the needle to the tissue area surrounding the mass, and the balloon is then inflated to identify the location of the mass. The needle can then be withdrawn. The inflated balloon is felt by the surgeon to determine the location of the mass.

In another embodiment of the present invention, a needle is inserted adjacent the mass, typically during the x-ray mammography while the breast is under compression and then an anesthetizing agent is introduced. A catheter having a balloon member at the distalmost end is then inserted in the needle until the balloon is just inside the tip of the needle. Then the needle is withdrawn, typically while the breast is still under compression. The proximal end of the catheter is preferably connected to a removable valve (such as a check valve) and the balloon is inflated to enable the surgeon to determine the location of the mass.

The above and other objects of the present invention will become more apparent when reference is made to the

3 following description, taken in conjunction with the accompanying drawings.

BRIEF DESCRIPTION OF THE DRAWINGS

FIG. 1 is a perspective view of the mass localization device of the present invention;

FIG. 2 is a cross sectional view taken through line 2—2 of FIG. 1 and illustrating the inflatable balloon of the localization device in both inflated and deflated states;

FIG. 3 is a partial sectional view of the mass localization device of FIG. 1, and illustrating the inflatable balloon in its inflated state;

FIG. 6 is a cross sectional view of a modified form of the mass localization device of FIG. 2; and, FIG. 7 is a cross sectional view of another mass localization device according to the present invention.

DESCRIPTION OF THE PREFERRED EMBODIMENTS

Figure 4:
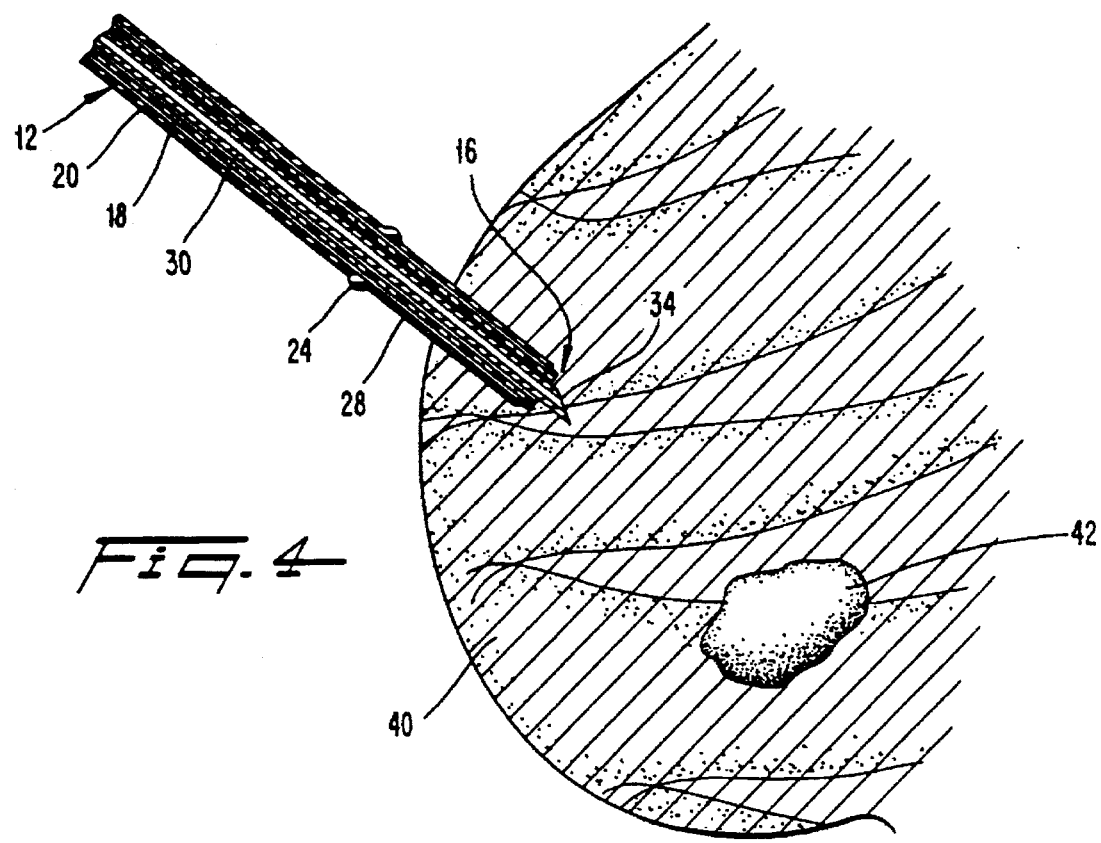
FIGS. 4 and 5 are exaggerated enlarged cross sectional views illustrating initial and final steps in employing the mass localization device of the present invention for locating a mass in breast tissue.

FIGS. 1–3 illustrate the mass localization device of the present invention, generally shown at 10. The localization device 10 includes a rubber catheter 12 having a proximal open end 14 and distal open end 16. The catheter 12 includes an inner wall 18 and an outer wall 20. The inner wall 18 and the outer wall 20 are connected together at proximal end 14 and distal end 16. Between the proximal end 14 and the distal end 16 is a gap 22 located between the inner wall 18 and the outer wall 20.

The inner wall 18 has a substantially uniform cross section along its entire length. The outer wall 20 includes a thickened ring 24 near the distal end 16 of the catheter, which separates the outer wall 20 into a proximal portion 26 and a distal portion 28. The proximal portion 26 has a greater thickness than the distal portion 28, which is more flexible for reasons described hereinafter.

A No. 25 gauge hollow needle 30 or the smallest gauge needle which is appropriate under the circumstances as will be apparent to one skilled in the art upon reading the present specification is provided having a hub 32 located at the proximal end of the needle 30, and a sharp open distal end 34. The needle 30 has a length slightly greater than the catheter 12. The catheter 12 has a length of 5, 10, 15, or 20 cm, depending on the size of the breast being operated on. The hollow needle 30 is insertable through the proximal end 14 of the catheter 12 so that the sharp distal end 34 extends slightly beyond the distal end 16 of the catheter 12.

The distal portion 28 of the outer wall 20 of catheter 12 forms an inflatable balloon at the distal end 16 of the catheter. A source of fluid, preferably a source of sterile air 33 or a source of a sterile saline solution or another liquid which preferably provides no side effects in case of a rupture of the balloon such as methylene blue, is communicated to the balloon 28 via a port 36 provided by a port extension 38 which attaches, or preferably is formed as part of the outer wall 20 of catheter 12. Upon supply of fluid through port 36, the balloon 28 expands to the position illustrated in FIG. 3, and illustrated in FIG. 2 in phantom at 28'. A preferred diameter of the balloon 28 is 2 to 5 cm. The thickened ring 24 allows only the balloon 28 to expand, rather than both the balloon 28 and the proximal portion 26 of the outer wall 20. When no supply of fluid is connected to port 36, for expanding the balloon 28, the balloon 28 maintains a flush relationship with the periphery of the catheter 12 as illustrated in FIGS. 1 and 2.

In use, the mass localization device 10 is inserted into body tissue under x-ray control to be adjacent to a mass in the tissue. Once the distal end of the device 10 is located proximate to the mass, local anaesthesia is supplied through needle 30 to the area adjacent the mass. The balloon 28 is then expanded to identify the location of the mass, and the needle 30 is removed. Thereafter, a surgeon can feel the location of the inflated balloon and form an incision from a point on the skin located closest to the balloon so as to make as small an incision as possible to gain access to the mass.

Figure 5:
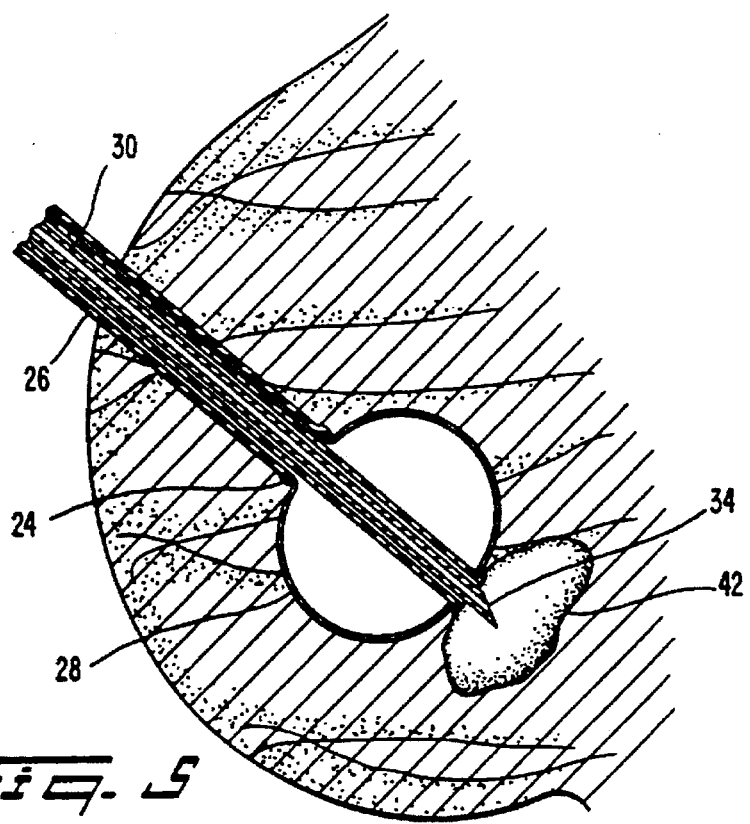

FIGS. 4 and 5 illustrate a localization technique for non-palpable breast masses employing the localization device 10 of the present invention. Initially, the needle 30 is inserted through the catheter 12 so that the distal end of the needle extends slightly beyond the distal end 16 of the catheter 12. Under x-ray control, the localization device 10 is inserted into the breast tissue 40 and maneuvered towards a mass 42 as illustrated in FIG. 4. The device 10 is carefully moved towards the mass 42 so that the distal end 16 of the catheter 12 is proximate the mass 42 as illustrated in FIG. 5. At this point, local anesthetic is injected through the needle 30 to the suspicious area. Thereafter, the supply of fluid 33 is connected to the port 36 for inflating the balloon 28 to the position shown in FIG. 5. Now, the mass 42 is palpable since a surgeon can feel the mass 42 through the skin by feeling for the inflated balloon 28. The needle 30 is then withdrawn from the catheter 12 and the patient is prepared for a surgical biopsy or other procedure with the catheter left in place. As a result, the surgeon forms an incision which accurately provides for the most direct access (or the most appropriate access) to the mass so that the surgeon can take a biopsy of the suspicious area.

With reference now to FIG. 6, a valve 50 is preferably provided at one end of the port extension 38. The valve 50 is preferably a suitable, conventional check valve which enables the catheter 20 to be supplied with fluid such as by inserting a needle of a syringe into the check valve and pushing the plunger into the syringe. Upon withdrawal of the needle of the syringe from the check valve 50, the pressurized fluid would remain in the catheter to maintain the balloon 28 in an inflated condition. The syringe may then be reinserted into the check valve 50 to provide additional fluid under pressure or to remove fluid under pressure. The fluid under pressure would be removed by withdrawing the plunger while the needle of the syringe is inserted in the check valve. In this way, the check valve and the syringe permit the balloon at the end of the catheter to be inflated, maintained in an inflated condition, and deflated as desired.

In addition, the catheter 20 is covered by a sheath 52 which is preferably made of latex. The sheath 52 covers the catheter from the distal end 16 of the catheter to the port extension 38. In this way, the sheath facilitates insertion of the catheter into the body tissue and prevents or minimizes any crimping of the inflatable balloon. If desired, after proper insertion of the catheter has been achieved, the sheath may be torn apart adjacent the extension port and withdrawn from the catheter. As the sheath is progressively pulled rearwardly and torn, the sheath is gradually removed from the catheter completely. Alternatively, the sheath may be torn apart and withdrawn only enough to uncover the balloon at the distal portion of the catheter. The sheath is preferably of a suitable, conventional form and may be provided with a weakened portion, such as a perforation running along the length of the sheath, to facilitate the tearing of the sheath.

With reference now to FIG. 7, another embodiment of a mass localization device according to the present invention includes a needle 60. The needle 60 preferably has a length which is appropriate for the distance that the needle is to be inserted into the breast or other body tissue. Typically, needles of various lengths will be available for use in connection with the present invention with the needles having a length of about 5 centimeters to about 25 centimeters.

The needle 60 has a sharp point to facilitate insertion of the needle into the breast or body tissue. The needle 60 also has an internal diameter which is sufficient to pass a catheter 64 having a balloon 66 which may be inflated so as to have a diameter of about 2 to 5 centimeters or more. As shown in FIG. 7, the balloon is generally spherical and is arranged symmetrically about a circumference of the distal end of the tubing and the balloon is also arranged symmetrically about a longitudinal axis of the tubing.

The needle 60 may be connected to a syringe (not shown) by a suitable, conventional hub 61. For example, the hub 61 may be threaded so as to threadably connect with a corresponding portion of the syringe. When the needle 60 is connected to a syringe, an anesthetizing agent or another fluid may be injected through the needle as desired. The syringe is removable from the needle as described more fully below to facilitate the insertion of the catheter 64 through the needle.

With the syringe removed (and after the needle has been inserted into the breast tissue with the tip of the needle at the mass to be localized), the catheter is inserted into the needle until the balloon 66 which is provided at the distal end 68 of the catheter 64 is just within the tip of the needle 60. A mark 70 is provided on the catheter at a location which indicates that the balloon 66 is just within the tip of the needle. Preferably, the mark is located at the rearwardmost end of the hub 61 when the balloon is just within the tip of the needle 60.

If the catheter is sufficiently rigid, the catheter may be inserted into the needle without the use of a stylette. However, if the catheter is not sufficiently rigid, insertion of the catheter into the needle may be facilitated by providing a stylette 72 inside the catheter. The stylette 72 has a blunt tip so as not to perforate the balloon 66.

When a stylette is used, the stylette 72 and the catheter 64 are inserted into the needle 60 as a unit. After the catheter is properly inserted into the needle, the needle is removed by withdrawing the needle over the catheter 64. In order to permit the needle to be withdrawn, the catheter should have a length which is slightly more than twice as long as the needle and the hub 61. If a stylette was used, the stylette is then removed by withdrawing the stylette from the catheter. If desired, the stylette may be removed prior to withdrawing the needle from the catheter.

After the needle and stylette have been withdrawn from the catheter, the catheter is supplied with a pressurized fluid to inflate the balloon as described above in connection with FIGS. 1–5. Preferably, a valve, especially a check valve as described above, is provided between the end of the catheter and the supply of pressurized fluid so as to enable the balloon to be readily inflated, maintained in an inflated condition and then deflated as desired.

If the valve would obstruct the removal of the needle from the catheter, the valve should be releasably connected to the catheter. In this way, the valve may be disconnected from the catheter until after the needle has been removed and the balloon is ready to be inflated.

The valve may be releasably connected to the catheter by a coupling 76 which is received by the proximal end of the catheter. The coupling 76 includes a portion which may be tapered or provided with a series of ridges so as to be frictionally retained within the catheter after insertion. Upon the use of sufficient force, however, the valve may be removed from the catheter by pulling the coupling 76 out of the proximal end of the catheter.

The valve may be supplied with fluid under pressure as described above in connection with FIG. 6. In this way, a syringe may be inserted into the valve and the plunger depressed to inflate the balloon. Upon withdrawal of the syringe from the valve, the balloon will remain inflated to anchor the catheter in the body tissue where desired.

In use, the needle of the mass localization device according to FIG. 7 is inserted into the breast or other tissue preferably while the breast is undergoing x-ray mammography and is under compression. The needle is inserted until the tip of the needle is at the mass to be localized. Then an anesthetizing agent is injected into the body tissue such as by a syringe which is releasably connected to the needle. The syringe is then disconnected from the needle and a catheter is inserted into the needle. Insertion of the catheter may be facilitated by the use of a stylette which is provided inside the catheter. When the catheter has been positioned with the balloon (at the end of the catheter) just within the tip of the needle, the needle is withdrawn and then the stylette is withdrawn. The catheter is then supplied with a sterile fluid to inflate the balloon as desired.

While the localization of breast masses has been specifically described, it is envisioned that the present invention can be employed for localizing masses in various other tissue environments.

The above description is intended by way of example only, and is not intended to limit the present invention in any way except as set forth in the following claims.

I claim:

1. A medical apparatus for localizing and palpating a mass in body tissue, comprising:

a tubing having an open proximal end and an open distal end, said tubing including an inner wall extending along the entire length of said tubing and an outer wall forming an external sheathing and being spaced from said inner wall and extend along the entire the entire length of said tubing, said inner wall and said outer wall being connected together at said distal end and proximal end of said tubing, said outer wall including a thickened portion to separate said outer wall into a proximal portion and a distal portion, said proximal portion having a thickness greater than a thickness of said distal portion, and said distal portion of said outer wall forming said expandable balloon portion with a gap formed between said inner wall and said outer wall extending along substantially the entire length of said tubing and communicating with said distal portion which forms said expandable balloon portion;

an expandable balloon portion positioned at a distalmost portion of said distal end of said tubing, said balloon portion being expandable at said distalmost portion of said tubing at a mass located deeply in the body tissue so as to be palpable through the body tissue; and a hollow needle having proximal and distal ends, said distal end being sharp, said needle being insertable through said proximal end of said tubing so that said distal end of said needle extends beyond said distal end of said tubing, with means for preventing the distal end of said needle from extending more than slightly beyond said distal end of said tubing.

2. The apparatus of claim 1, further comprising means for supplying fluid to said balloon portion, said balloon portion being expandable upon receiving said fluid.

3. A medical apparatus for localizing and palpating a mass in body tissue, comprising:

a tubing having an open proximal end and an open distal end, said tubing including an inner wall extending along the entire length of said tubing, and an outer wall spaced from said inner wall and extending along the entire length of said tubing, said inner wall and said outer wall being connected at said proximal end and said distal end of said tubing, a gap created between said inner wall and said outer wall extending substantially the entire length of said tubing, said outer wall including distinct proximal and distal portions, said distal portion forming an inflatable balloon with said inflatable balloon being located at a distalmost end of said tubing;

a needle having proximal and distal ends, said distal end being sharp, said needle being insertable through said proximal end of said tubing so that said distal end of said needle extends beyond said distal end of said tubing, with means for preventing said distal end of said needle from extending more than slightly beyond said distal end of said tubing; and means for supplying fluid to said inflatable balloon via said gap between said inner and outer walls of said tubing, said inflatable balloon being expanded upon receiving said supply of fluid to identify the location of a mass by positioning said tubing with said needle located therein adjacent to the mass in the body tissue so as to be palpable through the body tissue.

4. The apparatus of claim 3, wherein said proximal portion of said outer wall has a first thickness, and said distal portion of said outer wall has a second thickness, said first thickness being greater than said second thickness for ensuring that said distal portion of said outer wall expands upon supply of fluid to said inflatable balloon.

5. The apparatus of claim 3, further comprising a thickened ring member at an interface of said proximal portion and said balloon of said outer wall for preventing said proximal portion from inflating with said balloon upon supply of fluid.

6. The apparatus of claim 3 wherein said inflatable balloon is integral with said outer wall of said tubing.

7. The apparatus of claim 6 further comprising a thickened ring member formed integrally with said outer wall at an interface of said proximal portion and said balloon of said outer wall for preventing said proximal portion from inflating with said balloon upon said supply of fluid.

* * * * *